United States Patent
Ramsden et al.

(10) Patent No.: US 12,291,507 B2
(45) Date of Patent: May 6, 2025

(54) COMPOUNDS AND THEIR USE FOR THE TREATMENT OF ALPHA1-ANTITRYPSIN DEFICIENCY

(71) Applicant: CENTESSA PHARMACEUTICALS (UK) LIMITED, Altrincham (GB)

(72) Inventors: Nigel Ramsden, Cambridge (GB); David John Fox, Coventry Warwickshire (GB); James Andrew Huntington, Cheshire (GB); James Michael Tomlinson, Babraham Cambridge (GB)

(73) Assignee: CENTESSA PHARMACEUTICALS (UK) LIMITED, Altrincham (GB)

( * ) Notice: Subject to any disclaimer, the term of this patent is extended or adjusted under 35 U.S.C. 154(b) by 406 days.

(21) Appl. No.: 17/839,241

(22) Filed: Jun. 13, 2022

(65) Prior Publication Data

US 2023/0096524 A1 Mar. 30, 2023

Related U.S. Application Data

(63) Continuation of application No. PCT/GB2020/053194, filed on Dec. 11, 2020.

(30) Foreign Application Priority Data

Dec. 13, 2019 (GB) ...................................... 1918414

(51) Int. Cl.
C07D 239/54 (2006.01)
(52) U.S. Cl.
CPC .................................. C07D 239/54 (2013.01)
(58) Field of Classification Search
CPC ...................................................... C07D 239/54
See application file for complete search history.

(56) References Cited

U.S. PATENT DOCUMENTS

| | | | |
|---|---|---|---|
| 8,436,013 B2 | 5/2013 | Liu et al. | |
| 10,722,501 B2 | 7/2020 | Biber et al. | |
| 11,312,689 B2 * | 4/2022 | Ramsden | C07D 239/36 |
| 2016/0244415 A1 | 8/2016 | Furstner et al. | |
| 2018/0215731 A1 | 8/2018 | Crew et al. | |
| 2020/0361939 A1 | 11/2020 | Bandarage et al. | |

FOREIGN PATENT DOCUMENTS

| | | |
|---|---|---|
| JP | 2014169285 A | 9/2014 |
| WO | WO-2008143633 A2 | 11/2008 |
| WO | WO-2014096965 A2 | 6/2014 |
| WO | WO-2019243841 A1 | 12/2019 |
| WO | WO-2020081257 A1 | 4/2020 |
| WO | WO-2021116709 A1 | 6/2021 |

OTHER PUBLICATIONS

Senn, J Med Chem, 2017, vol. 60, 9585-9598. (Year: 2017).*
Berthelier et al. Discovery of an Inhibitor of Z-Alpha1 Antitrypsin Polymerization. PLoS One 10(5):e0126256 (May 11, 2015).
Bouchecareilh et al. Histone deacetylase inhibitor (HDACi) suberoylanilide hydroxamic acid (SAHA)-mediated correction of α1-antitrypsin deficiency. J Biol Chem 287(45):38265-38278 (2012).
Burrows et al. Chemical chaperones mediate increased secretion of mutant alpha 1-antitrypsin (alpha 1-AT) Z: A potential pharmacological strategy for prevention of liver injury and emphysema in alpha 1-AT deficiency. PNAS USA 97(4):1796-1801 (2000).
Certified Copy of GB1918414, Filed Dec. 13, 2022.
Chang et al. Small-molecule peptides inhibit Z alpha1-antitrypsin polymerization. J. Cell. Mol. Med. 13(8B):2304-2316 (2009).
Elliott et al. Topography of a 2.0 A structure of alpha1-antitrypsin reveals targets for rational drug design to prevent conformational disease. Protein Science 9:1274-1281 (2000).
GB1918414 Search Report dated May 22, 2020.
Gould et al. Salt Selection for Basic Drugs. Int J. Pharm. 33:201-217 (1986).
Huntington. How and why the Z variant of α1-antitrypson polymerises, and what can be done about it. 7th International Symposium on Serpin Biology, Structure and Function (Apr. 1, 2014).
Knaupp et al. Kinetic instability of the serpin Z alpha1-antitrypsin promotes aggregation. J. Mol. Biol. 396:375-383 (2010).
Mallya et al. Small molecules block the polymerization of Z alpha1-antitrypsin and increase the clearance of intracellular aggregates. J Med Chem 50(22):5357-5363 (2007).
Parfrey et al. Targeting a surface cavity of alpha 1-antitrypsin to prevent conformational disease. J. Biol. Chem. 278(35):33060-33066 (2003).
PCT/GB2020/053194 International Search Report and Written Opinion dated Feb. 1, 2021.

* cited by examiner

*Primary Examiner* — D Margaret M Seaman
(74) *Attorney, Agent, or Firm* — Wilson Sonsini Goodrich & Rosati

(57) ABSTRACT

The invention relates to specified benzamide compounds of formula (1), and pharmaceutical compositions containing the compounds. The compounds may be inducers of $\alpha_1$-antitrypsin (A1AT), and may be used in the treatment of a disease or disorder such as $\alpha_1$-antitrypsin deficiency (A1AD or AATD).

20 Claims, No Drawings

COMPOUNDS AND THEIR USE FOR THE TREATMENT OF ALPHA1-ANTITRYPSIN DEFICIENCY

CROSS-REFERENCE

This application is the by-pass continuation of International Application No. PCT/GB2020/053194, filed Dec. 11, 2020, which claims the benefit of GB Application No. 1918414.2, filed Dec. 13, 2019, each of which are incorporated herein by reference in their entireties.

The invention relates to certain benzamides and their medical use.

$\alpha_1$-Antitrypsin (A1AT) is a member of the serpin superfamily produced by the liver and secreted into the blood. It inhibits a variety of serine proteases, especially neutrophil elastase. When blood levels of A1AT are low, excessive neutrophil elastase activity degrades lung tissue resulting in respiratory complications such as chronic obstructive pulmonary disease (COPD).

The reference range of A1AT in blood is 0.9-2.3 g/L. Levels lower than this are typical of $\alpha_1$-antitrypsin deficiency (A1AD or AATD), a genetic disorder caused by mutations in the SERPINA1 gene, coding for A1AT. The Z mutation, the most common cause of AATD, is the substitution of glutamate to lysine at position 366 of A1AT (UniProtKB-P01009 (A1AT_HUMAN)), corresponding to position 342 in the mature protein (Z A1AT). The Z mutation affects the folding of A1AT resulting in only a small fraction acquiring the native/active state. The remainder is either cleared as misfolded protein or accumulates in the liver as stable polymers. As a consequence of the misfolding, homozygous carriers of the Z mutation (ZZ) have plasma levels of A1AT that are 10-15% of normal, predisposing carriers to COPD. Accumulation of Z A1AT polymers in liver cells predisposes carriers to cirrhosis, liver cancer and other liver pathologies.

The current treatment for the lung manifestation of AATD involves augmentation therapy using A1AT concentrates prepared from the plasma of blood donors. The US FDA has approved the use of four A1AT products: Prolastin, Zemaira, Glassia, and Aralast. Dosing is via once weekly intravenous infusion. Augmentation therapy has been demonstrated to slow progression of COPD. The liver manifestations of AATD (e.g. cirrhosis and cancer) are treated with steroids and liver transplantation. Investigational approaches to improved treatment of the liver manifestations include inhibition of Z A1AT polymerisation and increased clearance of polymers through the activation of autophagy. Investigational approaches to improved treatment of both the lung and the liver manifestations are directed towards improvement of Z A1AT folding and secretion.

Elliott et al (Protein Science, 2000, 9, 1274-1281) have described an X-ray crystal structure of A1AT and identified five cavities that are potential targets for rational drug design to develop agents that will affect Z A1AT polymerisation.

Parfrey et al (J. Biol. Chem., 2003, 278, 35, 33060-33066) have further defined a single cavity that is a potential target for rational drug design to develop agents that will affect Z A1AT polymerisation.

Knaupp et al (J. Mol. Biol., 2010, 396, 375-383) have shown that bis-ANS (4,4'-dianilino-1,1'-binaphthyl-5,5'-disulfonate) is able to bind to Z A1AT, but not to wild-type A1AT (M), with 1:1 stoichiometry and a $K_d$ of 700 nM.

Chang et al (J. Cell. Mol. Med., 2009, 13, 8B, 2304-2316) have reported a series of peptides, including Ac-TTAI-NH$_2$, that inhibit Z A1AT polymerization.

Burrows et al (Proc. Nat. Acad. Sci., 2000, 97, 4, 1796-1801) have shown that a series of non-selective chaperones, including 4-phenylbutyric acid, glycerol and trimethylamine oxide, are able to increase Z A1AT levels in cell supernatants and mouse models.

Bouchecareilh et al (Journal of Biological Chemistry, 2012, 287, 45, 38265-38278) describe the use of histone deacetylase inhibitors, in particular SAHA (suberoylanilide hydroxamic acid) to increase the secretion of both M and Z A1AT from cells.

Berthelier et al (PLOS ONE, May 11, 2015) have demonstrated that S-(4-nitrobenzyl)-6-thioguanosine is able to prevent Z A1AT polymerisation in vitro.

Mallya et al (J. Med. Chem., 2007, 50, 22, 5357-5363) describe a series of phenols, such as N-(4-hydroxy-3,5-dimethylphenyl)-2,5-dimethylthiophene-3-sulfonamide, able to block polymerisation of Z A1AT in vitro.

Huntington (XIIIth International Symposium on Proteinases, Inhibitors and Biological Control, 23 Sep. 2012, and 7$^{th}$ International Symposium on Serpin Biology, Structure and Function, 1 Apr. 2014) discussed a cavity from an X-ray crystal structure of Z A1AT that is a potential target for rational drug design to develop agents that will affect Z A1AT polymerisation.

U.S. Pat. No. 8,436,013B2 discloses a wide variety of structures able to increase secretion of Z A1AT from cells in the micromolar range.

WO2019/243841A1 discloses oxoindoline-4-carboxamide compounds as modulators of alpha-1-antitrypsin, and use in treating diseases associated with alpha-1-antitrypsin.

WO2020/081257A1 discloses pyrrolo-indazolyl-propanoic acid compounds as modulators of alpha-1-antitrypsin.

US2020/0361939A1 discloses further pyrrolo-indazolyl-propanoic acid compounds as modulators of alpha-1-antitrypsin.

According to one aspect of the present invention, there is provided a dioxo-dihydropyrimidinyl compound of formula (1)

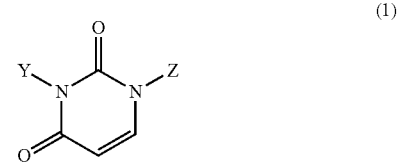

(1)

where:
One of Y or Z is H and the other of Y or Z is

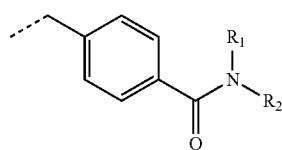

$R_1$ and $R_2$, are independently hydrogen or optionally substituted $C_1$-$C_6$ alkyl groups and
$R_1$ and $R_2$ may be fused to form a heterocycle,
and the compound of formula (1) is
4-((2,4-dioxo-3,4-dihydropyrimidin-1(2H)-yl)methyl)-N,N-dimethylbenzamide or 4-((2,4-dioxo-3,4-dihydropyrimidin-1(2H)-yl)methyl)-N-methylbenzamide or 4-((2,4-dioxo-3,4-dihydropyrimidin-1(2H)-yl)methyl)-N-isopropylbenzamide or 4-((2,4-dioxo-3,4-dihydropyrimidin-1(2H)-yl)methyl)-N-(4-fluorobenzyl)benzamide or 4-((2,6-dioxo-3,6-dihydropyrimidin-1(2H)-yl)methyl)-N,N-dimethylbenzamide or 4-((2,6-dioxo-3,6-dihydropyrimidin-1(2H)-yl)methyl)-N-ethyl-N-methylbenzamide or 4-((2,6-dioxo-3,6-dihydropyrimidin-1(2H)-yl)methyl)-N-isopropyl-N-methylbenzamide or N-benzyl-4-((2,6-dioxo-3,6-dihydropyrimidin-1(2H)-yl)methyl)-N-methylbenzamide or 4-((2,6-dioxo-3,6-dihydropyrimidin-1(2H)-yl)methyl)-N-methyl-N-(2,2,2-trifluoroethyl)benzamide.

Those skilled in the art will also understand that the compounds of the invention could be described as uracils.

We have found that compounds of the invention are shown surprisingly to be highly effective at increasing levels of correctly folded, and hence active, Z A1AT, whilst having no effect on the secretion of wild type (M)A1AT or of the Siiyama variant of A1AT.

The compound of the invention may be in a pharmaceutically acceptable salt form or crystalline form.

The term "pharmaceutically acceptable salt" refers to a pharmaceutically acceptable mono organic or inorganic salt of the compound of the invention. This may include addition salts of inorganic acids such as hydrochloride, hydrobromide, hydroiodide, sulphate, phosphate, diphosphate and nitrate or of organic acids such as acetate, maleate, fumarate, tartrate, succinate, citrate, lactate, methanesulphonate, p-toluenesulphonate, palmoate and stearate. Exemplary salts also include oxalate, chloride, bromide, iodide, bisulphate, acid phosphate, isonicotinate, salicylate, acid citrate, oleate, tannate, pantothenate, bitartrate, ascorbate, gentisinate, gluconate, glucuronate, saccharate, formate, benzoate, glutamate, ethanesulfonate, and benzenesulfonate salts. For other examples of pharmaceutically acceptable salts, reference can be made to Gould (1986, Int J Pharm 33: 201-217).

According to a further aspect of the invention, there is a provided a pharmaceutical composition comprising the compound of the invention as described herein and a pharmaceutically or therapeutically acceptable excipient or carrier.

The term "pharmaceutically or therapeutically acceptable excipient or carrier" refers to a solid or liquid filler, diluent or encapsulating substance which does not interfere with the effectiveness or the biological activity of the active ingredients and which is not toxic to the host, which may be either humans or animals, to which it is administered. Depending upon the particular route of administration, a variety of pharmaceutically acceptable carriers such as those well known in the art may be used. Non-limiting examples include sugars, starches, cellulose and its derivatives, malt, gelatin, talc, calcium sulfate, vegetable oils, synthetic oils, polyols, alginic acid, phosphate buffered solutions, emulsifiers, isotonic saline, and pyrogen-free water.

All suitable modes of administration are contemplated according to the invention. For example, administration of the medicament may be via oral, subcutaneous, direct intravenous, slow intravenous infusion, continuous intravenous infusion, intravenous or epidural patient controlled analgesia (PCA and PCEA), intramuscular, intrathecal, epidural, intra-cisternal, intraperitoneal, transdermal, topical, transmucosal, buccal, sublingual, transmucosal, inhalation, intranasal, intra-atricular, intranasal, rectal or ocular routes. The medicament may be formulated in discrete dosage units and can be prepared by any of the methods well known in the art of pharmacy.

All suitable pharmaceutical dosage forms are contemplated. Administration of the medicament may for example be in the form of oral solutions and suspensions, tablets, capsules, lozenges, effervescent tablets, transmucosal films, suppositories, buccal products, oral mucoretentive products, topical creams, ointments, gels, films and patches, transdermal patches, abuse deterrent and abuse resistant formulations, sterile solutions suspensions and depots for parenteral use, and the like, administered as immediate release, sustained release, delayed release, controlled release, extended release and the like.

Another aspect of the invention is the use of the compound of the invention as defined herein in the manufacture of a medicament for the treatment of a disease or disorder.

A further aspect of the invention is the compound of the invention for use as an inducer of Z A1AT secretion.

Further provided is the compound of the invention as defined herein for use in the treatment of a disease or disorder.

The invention also encompasses a method of treating a disease or disorder, comprising the step of administering the compound or the pharmaceutical composition of the invention as defined herein to a patient in need of same.

The invention further encompasses the use of a compound of the invention as an inducer of Z A1AT secretion. The use may be in the treatment of a disease or disorder. Additionally or alternatively, the use may be in vitro, for example in an in vitro assay.

A disease or disorder suitable for treatment according to the relevant aspects of the invention is one which is characterised by low plasma levels of A1AT, for example AATD.

The use of a numerical range in this description is intended unambiguously to include within the scope of the invention all individual integers within the range and all the combinations of upper and lower limit numbers within the broadest scope of the given range.

As used herein, the term "comprising" is to be read as meaning both comprising and consisting of. Consequently, where the invention relates to a "pharmaceutical composition comprising as active ingredient" a compound, this terminology is intended to cover both compositions in which other active ingredients may be present and also compositions which consist only of one active ingredient as defined.

Unless otherwise defined, all the technical and scientific terms used here have the same meaning as that usually understood by an ordinary specialist in the field to which this invention belongs. Similarly, all the publications, patent applications, all the patents and all other references mentioned here are incorporated by way of reference in their entirety (where legally permissible).

Particular non-limiting examples of the present invention will now be described.

EXPERIMENTAL

Example 1: 4-((2,4-dioxo-3,4-dihydropyrimidin-1(2H)-yl)methyl)-N,N-dimethylbenzamide 4-((2,4-dioxo-3,4-dihydropyrimidin-1(2H)-yl)methyl)-N,N-dimethylbenzamide was prepared using the following sequential synthesis procedures.

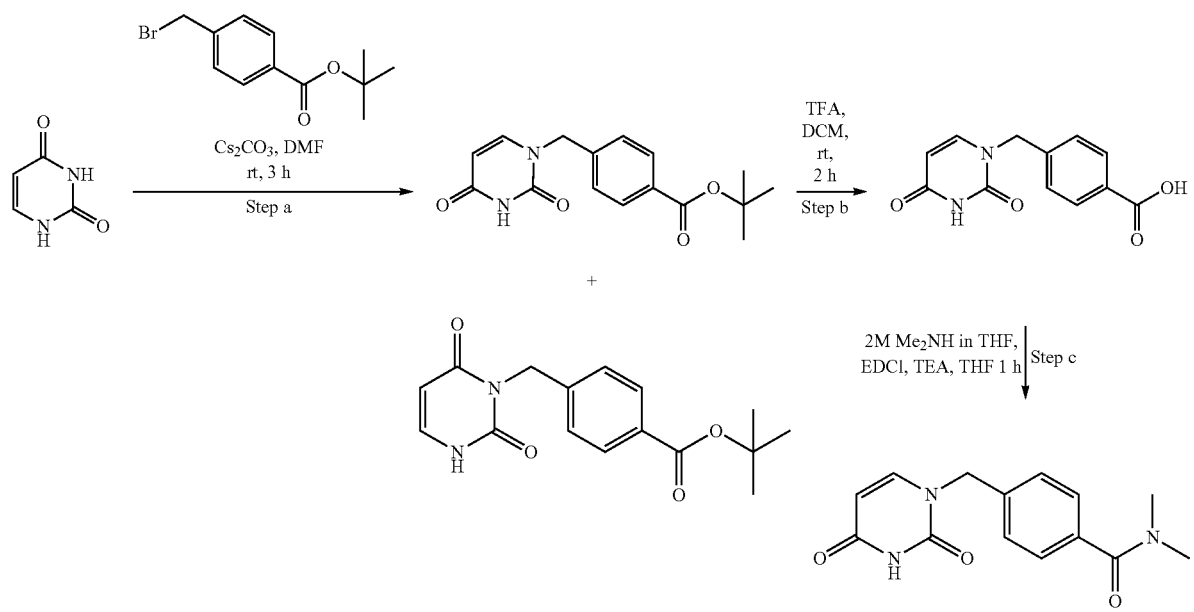 [SMILES: CC(C)(C)OC(=O)c1ccc(CBr)cc1 ; O=c1cc[nH]c(=O)[nH]1 ; CC(C)(C)OC(=O)c1ccc(Cn2ccc(=O)[nH]c2=O)cc1 ; O=C(O)c1ccc(Cn2ccc(=O)[nH]c2=O)cc1 ; CC(C)(C)OC(=O)c1ccc(Cn2c(=O)cc[nH]c2=O)cc1 ; CN(C)C(=O)c1ccc(Cn2ccc(=O)[nH]c2=O)cc1]

Step a—Synthesis of tert-butyl 4-((2,4-dioxo-3,4-dihydropyrimidin-1(2H')-yl)methyl)benzoate Uracil (5 g) and caesium carbonate (50.85 g) were stirred in dimethylformamide (50 ml) for 10 minutes at room temperature. Tert-butyl 4-(bromomethyl)benzoate (14.11 g) was added and the reaction was stirred for 3 hours. The reaction was diluted with water and the resulting yellow precipitate collected by filtration. The crude product was purified by column chromatography on silica, eluting with ethyl acetate/hexane (30% to 50%) to give tert-butyl 4-((2,4-dioxo-3,4-dihydropyrimidin-1(2H)-yl)methyl)benzoate (3.5 g, most polar product) and tert-butyl 4-((2,6-dioxo-3,6-dihydropyrimidin-1(2H)-yl)methyl)benzoate (420 mg, least polar product).

Step b—Synthesis of 4-((2-dioxo-3,4-dihydropyrimidin-1(2H)-yl)methyl)benzoic acid Tert-butyl 4-((2,4-dioxo-3,4-dihydropyrimidin-1(2H)-yl)methyl)benzoate (3 g) was dissolved in dichloromethane (20 ml) and trifluoroacetic acid (30 ml) was added slowly. The reaction was stirred for 3 hours at room temperature. The reaction was concentrated under reduced pressure and the resulting oil stirred with diethyl ether (100 ml) for 20 minutes at room temperature. The resultant solid was collected by filtration, washed with diethyl ether (2×30 ml) and dried in vacuo to give 4-((2,4-dioxo-3,4-dihydropyrimidin-1(2H)-yl)methyl)benzoic acid.

Step c—Synthesis of 4-((2,4-dioxo-3,4-dihydropyrimidin-1(2H)-yl)methyl)-N,N-dimethylbenzamide 4-((2,4-dioxo-3,4-dihydropyrimidin-1(2H)-yl)methyl)benzoic acid (64 mg, 0.27 mmol) and N-(3-dimethylaminopropyl)-N'-ethylcarbodiimide hydrochloride (86 mg, 0.54 mmol) were stirred in tetrahydrofuran (1 ml) for 10 minutes at 0° C. under nitrogen. The reaction was then allowed to warm to room temperature. Triethylamine (0.11 ml, 81 mmol) and dimethylamine (2M solution in tetrahydrofuran, 69 mmol) were added and the reaction was stirred for 2 hours. The reaction was concentrated under reduced pressure and the residue columned on silica eluting with 4% methanol in dichloromethane. Product containing fractions were concentrated to give 4-((2,4-dioxo-3,4-dihydropyrimidin-1(2H)-yl)methyl)-N,N-dimethylbenzamide.

m/z: 273.10

$^1$H NMR (400 MHz, d6 DMSO) δ 11.35, (1H, s), 7.78 (1H, d), 7.38 (2H, d), 7.32 (2H, d), 5.60 (1H, d), 4.90 (2H, s), 2.96-2.86 (6H, br).

Example 2: 4-((2,4-dioxo-3,4-dihydropyrimidin-1(2H)-yl)methyl)-N-methylbenzamide

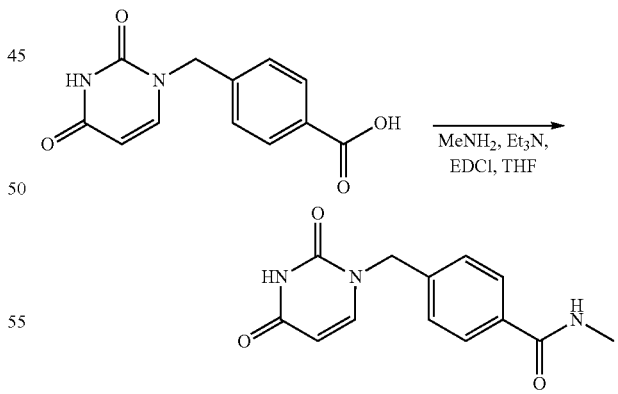

4-((2,4-dioxo-3,4-dihydropyrimidin-1(2H)-yl)methyl)-N-methylbenzamide was prepared similarly using methylamine instead of dimethylamine in step c.

m/z (M+Na): 282.08 (calc 282.08)

1H NMR (400 MHz, d6 DMSO) δ 11.34 (1H, s), 8.44-8.39 (1H, m), 7.84-7.74 (3H, m), 7.39-7.32 (2H, m), 5.61 (1H, dd), 4.91 (2H, s), 2.77 (3H, d).

Example 3: 4-((2,4-dioxo-3,4-dihydropyrimidin-1(2H)-yl)methyl)-N-isopropylbenzamide

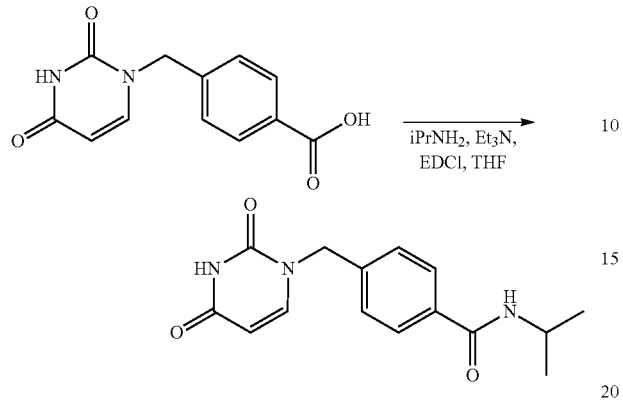

4-((2,4-dioxo-3,4-dihydropyrimidin-1(2H)-yl)methyl)-N-isopropylbenzamide was prepared similarly using isopropylamine instead of dimethylamine in step c.

m/z (M+Na): 310.12 (calc 310.12)

1H NMR (400 MHz, d6 DMSO) δ 11.34 (1H, s), 8.18 (1H, d), 7.84-7.79 (2H, m), 7.77 (1H, d), 7.39-7.30 (2H, m), 5.61 (1H, dd), 4.91 (2H, s), 4.08 (1H, sept.), 1.15 (6H, d).

Example 4: 4-((2,4-dioxo-3,4-dihydropyrimidin-1(2H)-yl)methyl)-N-(4-fluorobenzyl)benzamide

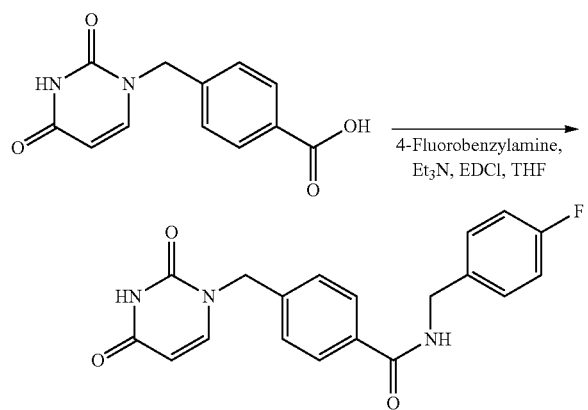

4-((2,4-dioxo-3,4-dihydropyrimidin-1(2H)-yl)methyl)-N-(4-fluorobenzyl)benzamide was prepared similarly using 4-fluorobenzylamine instead of dimethylamine in step c.

m/z (M+Na): 376.11 (calc 376.11)

1H NMR (400 MHz, d6 DMSO) δ 11.27 (1H, s), 9.04 (1H, t), 7.91-7.82 (2H, m), 7.77 (1H, d), 7.42-7.30 (4H, m), 7.18-7.10 (2H, m), 5.61 (1H, s), 4.92 (2H, s), 4.45 (2H, d).

Example 5: 4-((2,6-dioxo-3,6-dihydropyrimidin-1(2H)-yl)methyl)-N,N-dimethylbenzamide 4-((2,6-dioxo-3,6-dihydropyrimidin-1(2H)-yl)methyl)-N,N-dimethylbenzamide was prepared using the following sequential synthesis procedures.

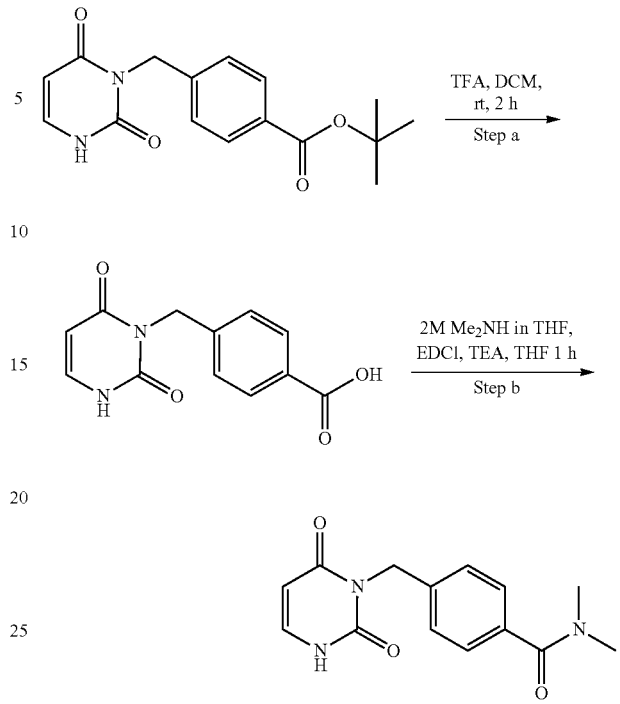

Step a—Synthesis of 4-((2,6-dioxo-3,6-dihydropyrimidin-1(2H)-yl)methyl)benzoic acid Tert-butyl 4-((2,6-dioxo-3,6-dihydropyrimidin-1(2H)-yl)methyl)benzoate (2 g) was dissolved in dichloromethane (10 ml) and trifluoroacetic acid (15 ml) was added slowly. The reaction was stirred for 3 hours at room temperature. The reaction was concentrated under reduced pressure and the resulting oil stirred with diethyl ether (50 ml) for 20 minutes at room temperature. The resultant solid was collected by filtration, washed with diethyl ether (2×15 ml) and dried in vacuo to give 4-((2,6-dioxo-3,6-dihydropyrimidin-1(2H)-yl)methyl)benzoic acid.

Step b—Synthesis of 4-((2,6-dioxo-3,6-dihydropyrimidin-1(2H)-yl)methyl)-N,N-dimethylbenzamide 4-((2,6-dioxo-3,6-dihydropyrimidin-1(2H)-yl)methyl)benzoic acid (32 mg) and N-(3-dimethylaminopropyl)-N'-ethylcarbodiimide hydrochloride (43 mg) were stirred in tetrahydrofuran (1 ml) for 10 minutes at 0° C. under nitrogen. The reaction was then allowed to warm to room temperature. Triethylamine (0.06 ml) and dimethylamine (2M solution in tetrahydrofuran) were added and the reaction was stirred for 2 hours. The reaction was concentrated under reduced pressure and the residue columned on silica eluting with 4% methanol in dichloromethane. Product containing fractions were concentrated to give 4-((2,6-dioxo-3,6-dihydropyrimidin-1(2H)-yl)methyl)-N,N-dimethylbenzamide.

m/z: 273.51 (calc 273.11)

1H NMR (400 MHz, d6 DMSO) δ 7.48 (1H, d), 7.32 (2H, d), 7.27 (2H, d), 5.61 (1H, d), 4.95 (2H, s), 2.95-2.85 (6H, br).

Example 6: 4-((2,6-dioxo-3,6-dihydropyrimidin-1(2H)-yl)methyl)-N-ethyl-N-methylbenzamide

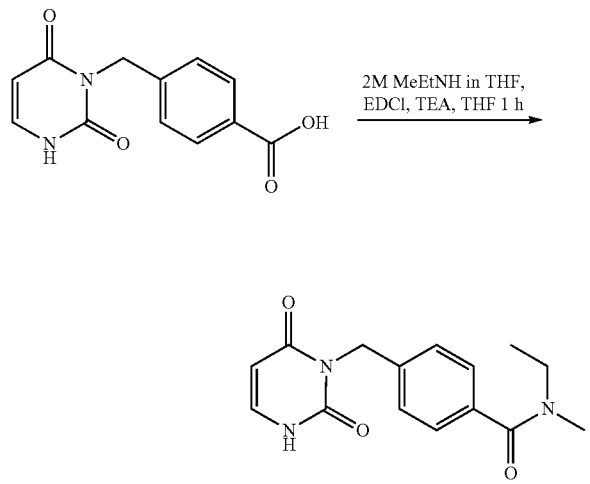 [SMILES: O=C(O)c1ccc(Cn2c(=O)cc[nH]c2=O)cc1 ; CCN(C)C(=O)c1ccc(Cn2c(=O)cc[nH]c2=O)cc1]

4-((2,6-dioxo-3,6-dihydropyrimidin-1(2H)-yl)methyl)-N-ethyl-N-methylbenzamide was prepared similarly using methylethylamine instead of dimethylamine in step b.

m/z: 287.18 (calc 287.13)

$^1$H NMR (400 MHz, d6 DMSO) δ 7.49 (1H, d), 7.28 (4H, br s), 5.64 (1H, d), 4.95 (2H, d), 3.4-3.2 (2H, m), 2.95-2.85 (3H, br), 1.1-1.0 (3H, br).

Example 7: 4-((2,6-dioxo-3,6-dihydropyrimidin-1(2H)-yl)methyl)-N-isopropyl-N-methylbenzamide

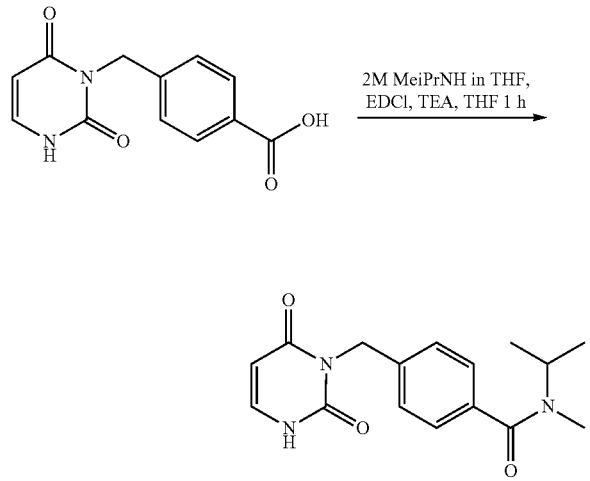 [SMILES: O=C(O)c1ccc(Cn2c(=O)cc[nH]c2=O)cc1 ; CC(C)N(C)C(=O)c1ccc(Cn2c(=O)cc[nH]c2=O)cc1]

4-((2,6-dioxo-3,6-dihydropyrimidin-1(2H)-yl)methyl)-N-isopropyl-N-methylbenzamide was prepared similarly using methylisopropylamine instead of dimethylamine in step b.

m/z: 301.18 (calc 301.14)

$^1$H NMR (400 MHz, d6 DMSO) δ 11.20 (1H, s), 7.49 (1H, d), 7.28 (4H, br s), 5.65 (1H, d), 4.95 (2H, d), 3.78 (2H, br m), 2.78-2.60 (3H, br), 1.2-1.0 (6H, br).

Example 8: N-benzyl-4-((2,6-dioxo-3,6-dihydropyrimidin-1(2H)-yl)methyl)-N-methylbenzamide

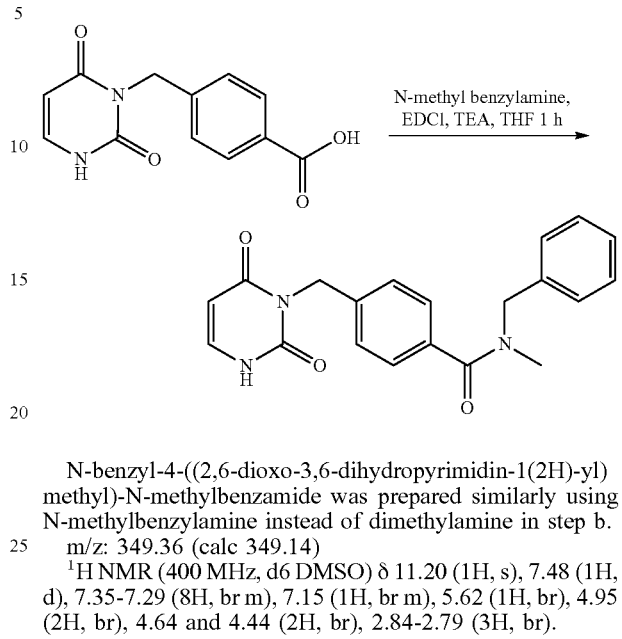

N-benzyl-4-((2,6-dioxo-3,6-dihydropyrimidin-1(2H)-yl)methyl)-N-methylbenzamide was prepared similarly using N-methylbenzylamine instead of dimethylamine in step b.

m/z: 349.36 (calc 349.14)

$^1$H NMR (400 MHz, d6 DMSO) δ 11.20 (1H, s), 7.48 (1H, d), 7.35-7.29 (8H, br m), 7.15 (1H, br m), 5.62 (1H, br), 4.95 (2H, br), 4.64 and 4.44 (2H, br), 2.84-2.79 (3H, br).

Example 9: 4-((2,6-dioxo-3,6-dihydropyrimidin-1(2H)-yl)methyl)-N-methyl-N-(2,2,2-trifluoroethyl)benzamide

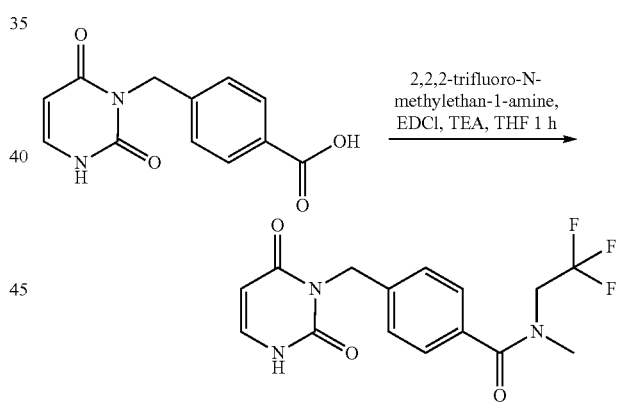

4-((2,6-dioxo-3,6-dihydropyrimidin-1(2H)-yl)methyl)-N-methyl-N-(2,2,2-trifluoroethyl)benzamide was prepared similarly using 2,2,2-trifluoro-N-methylethan-1-amine instead of dimethylamine in step b.

m/z: 341.10 (calc 341.10)

$^1$H NMR (400 MHz, d6 DMSO) δ 11.25 (1H, s), 7.49 (OH, d), 7.36-7.31 (4H, br m), 5.65 (1H, br), 4.96 (2H, s), 4.34 and 4.11 (2H, br), 3.00 (3H, br).

Example 10: Activity of Compounds of the Invention in an A1AT Cell Secretion Assay Using HEK-Z Cells

Methods

HEK-Z cells, a human embryonic kidney cell line stably transfected with the human Z A1AT gene, were plated into 96 well plates ($3.0 \times 10^5$ cells/ml with 200 μl of media/well) overnight at 37° C. in a humidified atmosphere containing 5% $CO_2$. Following incubation cells were washed with 200 μl serum-free media three times and media was replaced with treatments in quadruplicate using serum free media containing either vehicle, 10 μM suberanilohydroxamic acid (SAHA) or a compound of the invention (at concentrations of 10, 33, 100 and 333 nM) for 48 h in a 37° C. incubator in a final volume of 200 μl. At the end of the incubation step the supernatants were removed from the wells, centrifuged at 1000×g at 4° C. for 10 min and were assayed for human A1AT levels by ELISA (Human Serpin A1/$\alpha_1$-antitrypsin duo set ELISA, R& D Systems, DY1268) per manufacturer's instructions.

Briefly, a 96 well plate was coated with human A1AT capture antibody overnight at room temperature (1:180 dilution from stock, 100 μl final volume/well). The capture antibody was then removed and wells washed three times with 300 μl wash buffer (0.05% Tween 20 in PBS) and then 200 μl reagent diluent (25% Tween 20 in PBS) was incubated in each well for 1 h at room temperature. Diluted samples, standards (125, 250, 500, 1000, 2000, 4000 and 8000 pg/ml A1AT) or blanks were then added to each well in duplicate and the plates were covered with a plate sealer and left at room temperature for 2 h. At the end of the sample incubation step, samples were removed and all wells washed as previously and 100 μl detection antibody (1:180 dilution from stock) was added to each well and incubated for a further 2 h at room temperature. Following incubation with detection antibody, supernatant was removed and wells were washed as previously and 100 μl streptavidin-HRP solution (1:200 dilution from stock) was added to each well for 20 min in the dark. After which, 50 μl stop solution (2M $H_2SO_4$) was added and optical density (OD) of each well was read at 450 nm with 570 nm blank subtracted from each well using a microplate reader. A 4-parameter logistic curve was constructed using GraphPad Prism 7 and A1AT concentrations were determined in each sample by interpolation from a standard curve and multiplying by the appropriate dilution factor.

Results

The data in Table 1 show that compounds of Examples 1-9 increase secretion of Z A1AT from HEK-Z cells at 300 nM.

TABLE 1

| Example | Median A1AT % increase over vehicle at 300 nM |
|---|---|
| 1 | 130 |
| 2 | 175 |
| 3 | 190 |
| 4 | 170 |
| 5 | 140 |
| 6 | 190 |
| 7 | 170 |
| 8 | 175 |
| 9 | 180 |

The invention claimed is:

1. A compound represented by the structure:

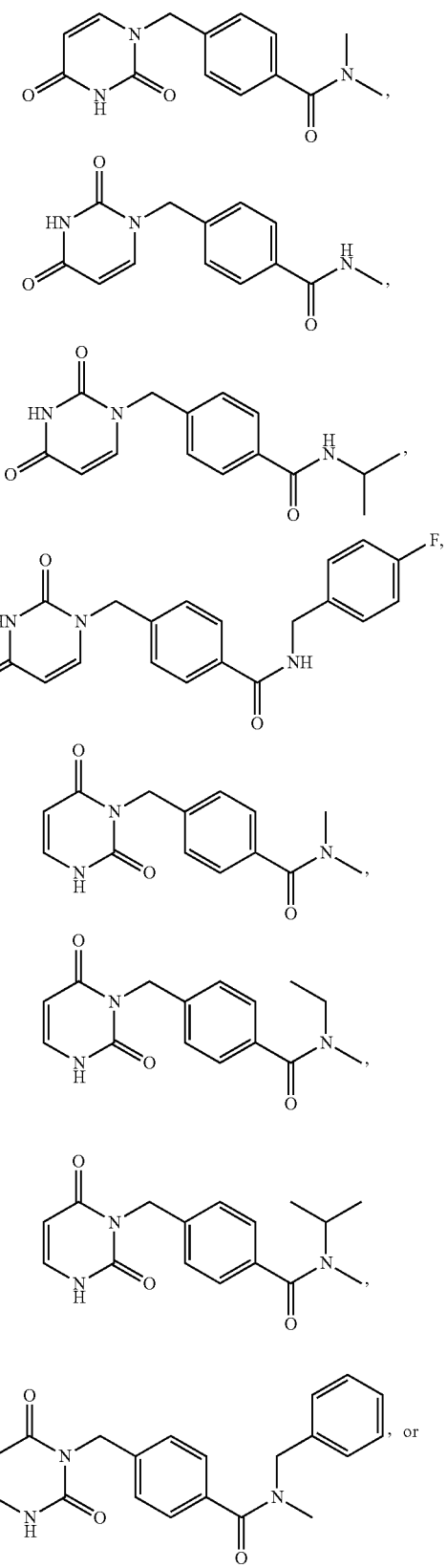

-continued

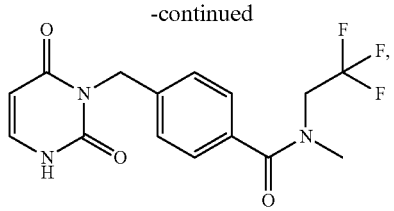

or a pharmaceutically acceptable salt of any one thereof.

2. The compound of claim 1, wherein the compound is in a crystal form.

3. A pharmaceutical composition comprising a compound represented by the structure:

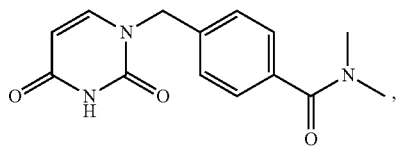

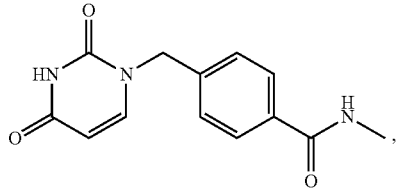

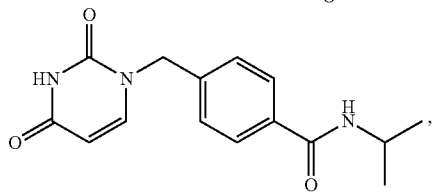

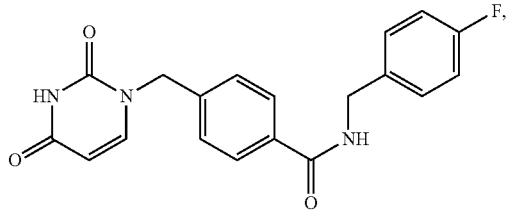

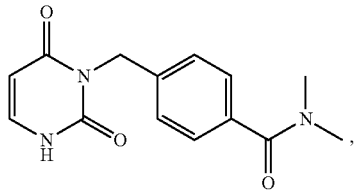

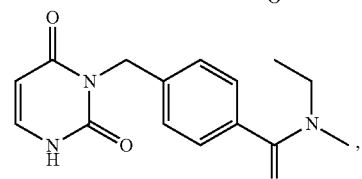

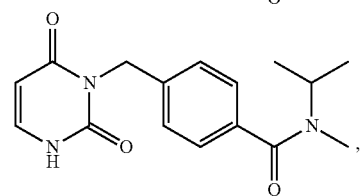

-continued

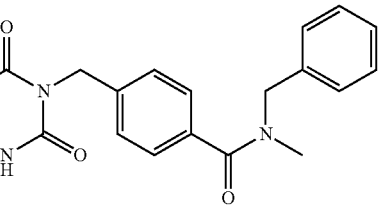, or

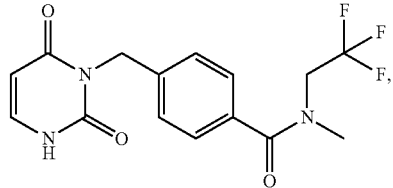

or a pharmaceutically acceptable salt of any one thereof, and a pharmaceutically acceptable of carrier.

4. A method of inducing Z A1AT secretion in a subject in need thereof, comprising administering to the subject a compound represented by the structure:

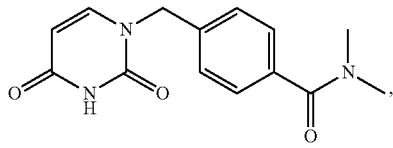

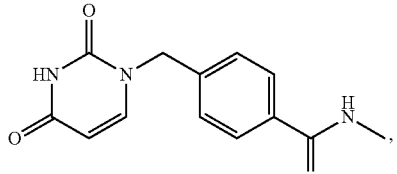

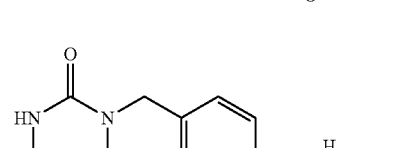

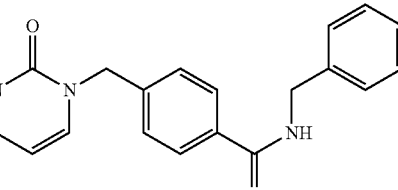

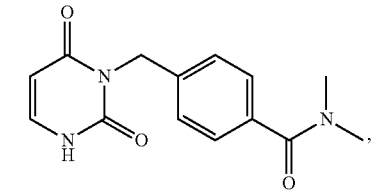

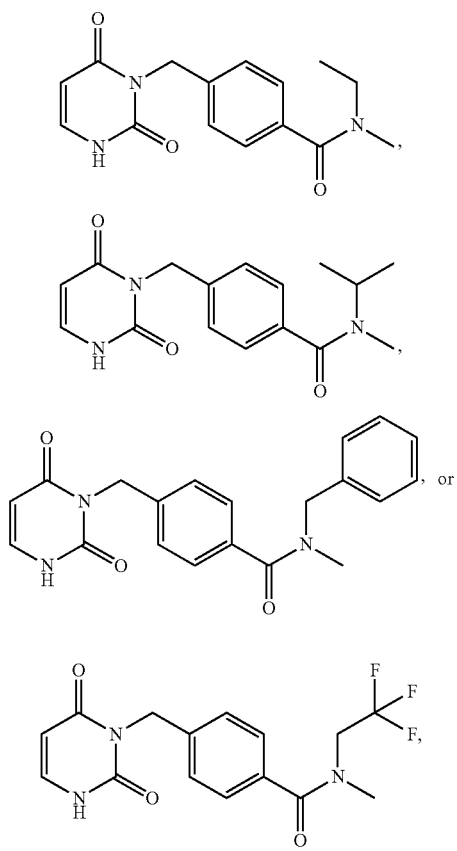
or a pharmaceutically acceptable salt of any one thereof.
5. The compound of claim 1, wherein the compound is represented by:
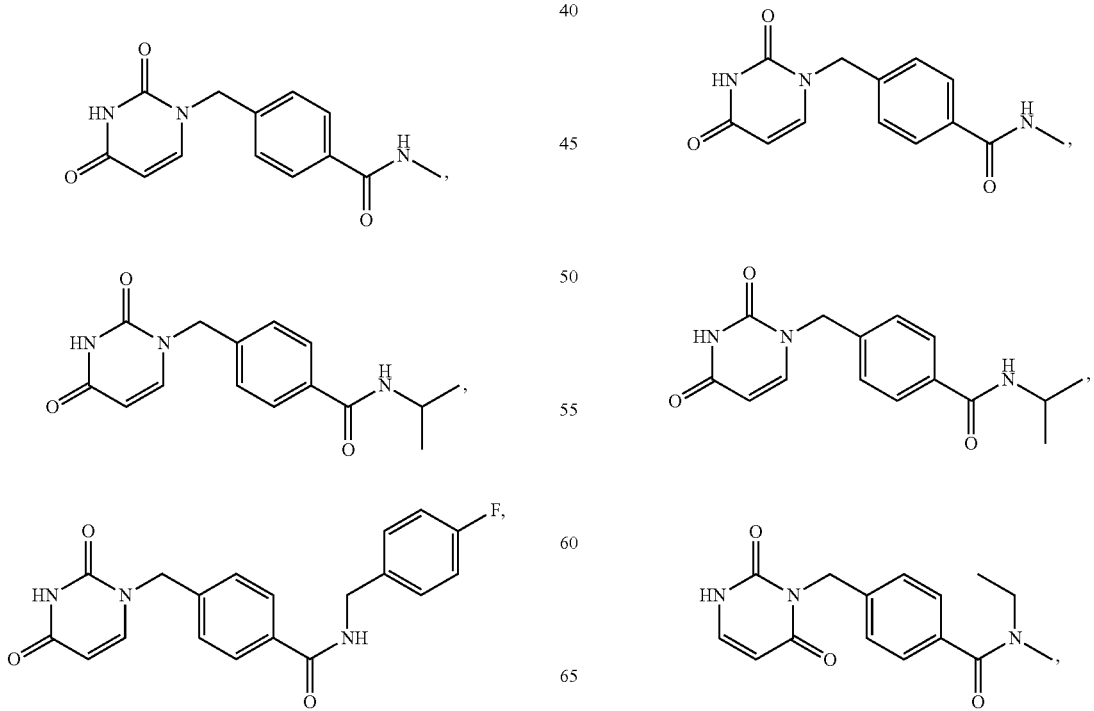
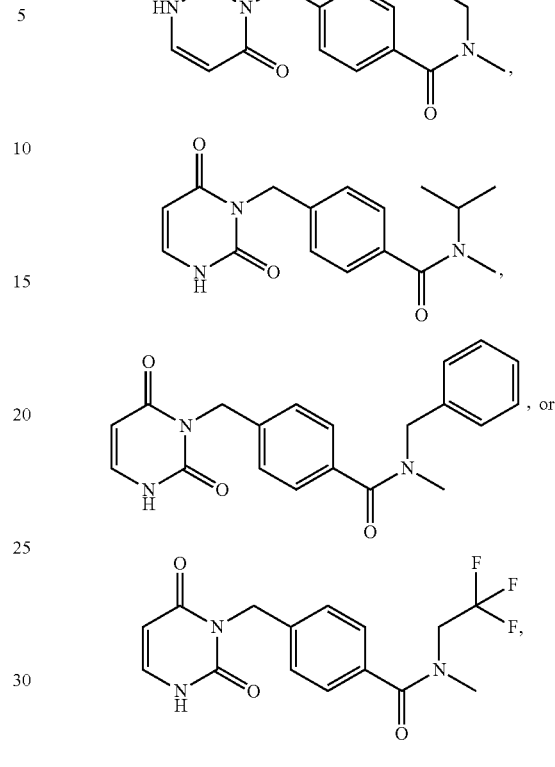
or a pharmaceutically acceptable salt of any one thereof.
6. The compound of claim 5, wherein the compound is represented by:

-continued

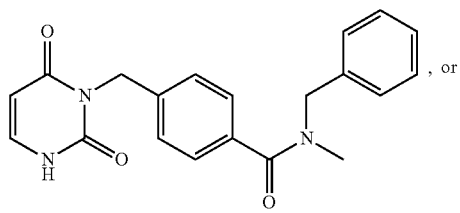, or

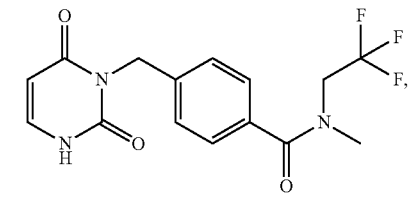

or a pharmaceutically acceptable salt of any one thereof.

7. The compound of claim 6, wherein the compound is represented by:

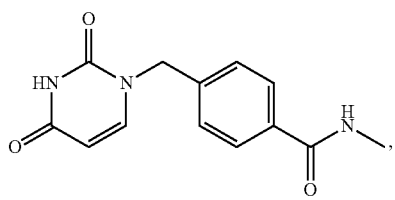 [SMILES: CNC(=O)c1ccc(Cn2ccc(=O)[nH]c2=O)cc1]

or a pharmaceutically acceptable salt thereof.

8. The compound of claim 6, wherein the compound is represented by:

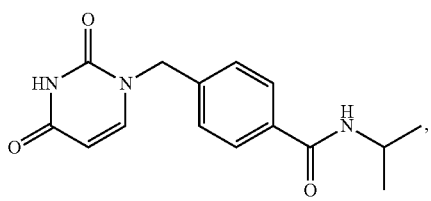 [SMILES: CC(C)NC(=O)c1ccc(Cn2ccc(=O)[nH]c2=O)cc1]

or a pharmaceutically acceptable salt thereof.

9. The compound of claim 6, wherein the compound is represented by:

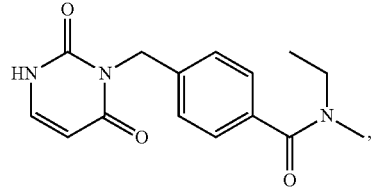 [SMILES: CCN(C)C(=O)c1ccc(Cn2c(=O)cc[nH]c2=O)cc1]

or a pharmaceutically acceptable salt thereof.

10. The compound of claim 6, wherein the compound is represented by:

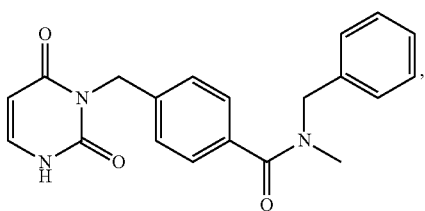 [SMILES: CN(Cc1ccccc1)C(=O)c1ccc(Cn2c(=O)cc[nH]c2=O)cc1]

or a pharmaceutically acceptable salt thereof.

11. The compound of claim 6, wherein the compound is represented by:

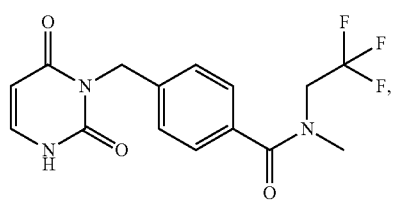

or a pharmaceutically acceptable salt thereof.

12. The pharmaceutical composition of claim 3, wherein the compound is represented by:

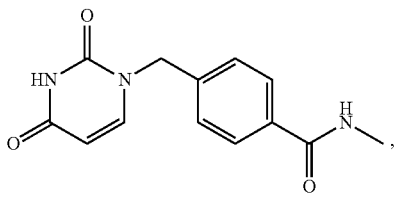

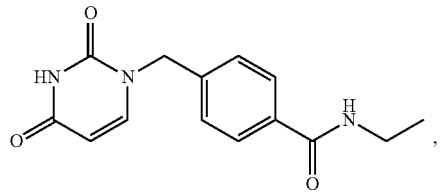

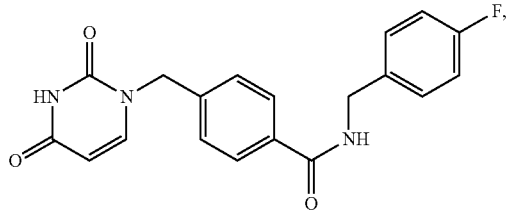

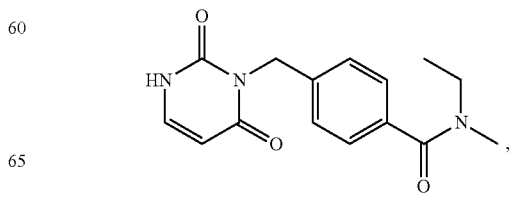

-continued
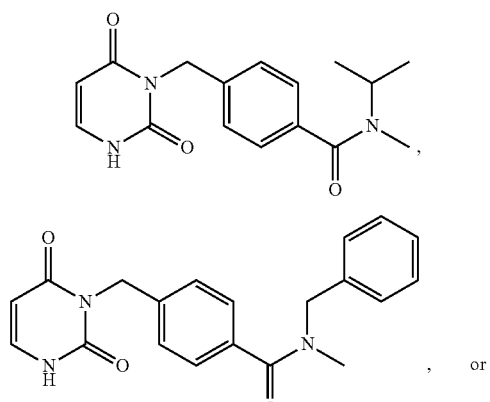
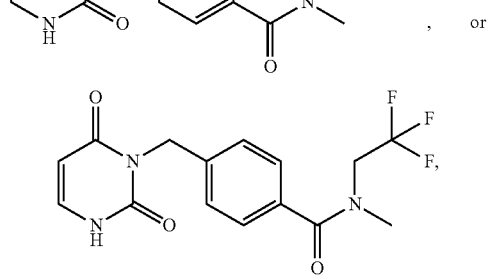
or a pharmaceutically acceptable salt of any one thereof.
13. The pharmaceutical composition of claim 12, wherein the compound is represented
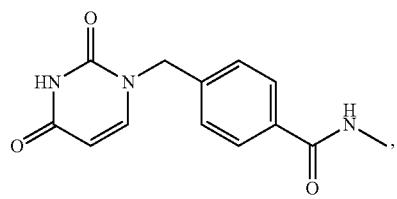
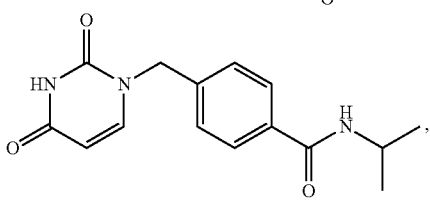
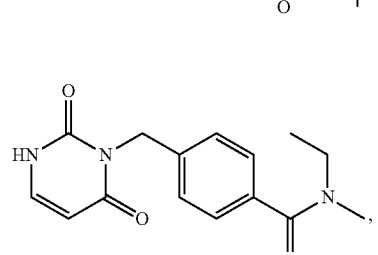
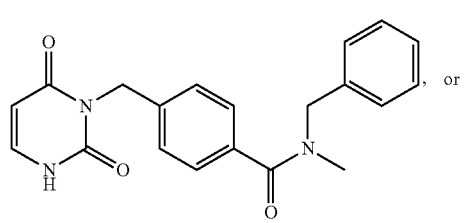
-continued
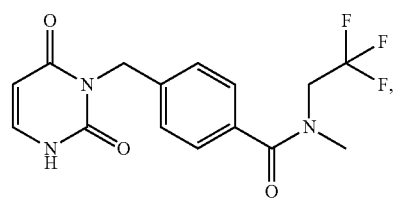 [SMILES: CN(CC(F)(F)F)C(=O)c1ccc(Cn2c(=O)cc[nH]c2=O)cc1]
or a pharmaceutically acceptable salt of any one thereof.
14. The method of claim 4, wherein the compound is represented by:
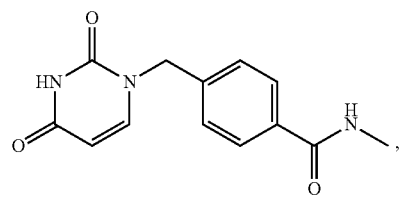
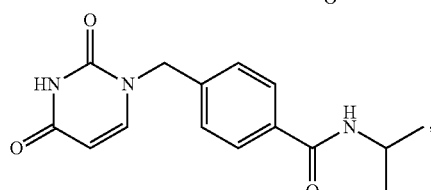
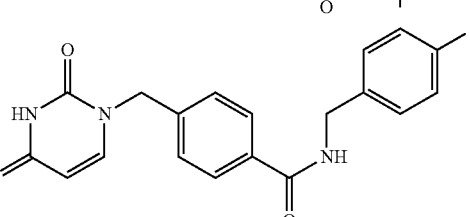
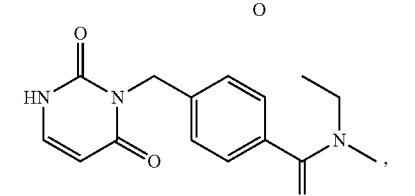
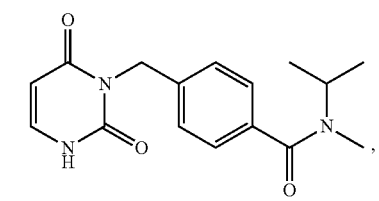
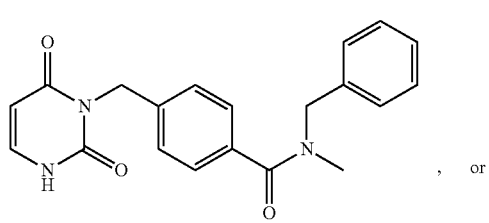

-continued

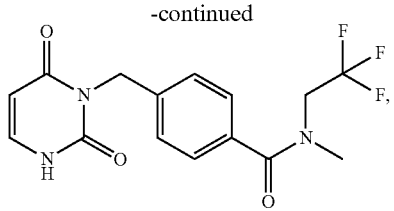

or a pharmaceutically acceptable salt of any one thereof.

15. The method of claim 14, wherein the compound is represented by:

[structures]

or a pharmaceutically acceptable salt of any one thereof.

16. The method of claim 15, wherein the compound is represented by:

[structure]

or a pharmaceutically acceptable salt thereof.

17. The method of claim 15, wherein the compound is represented by:

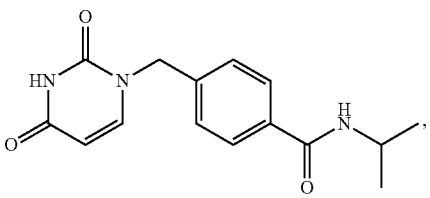 [SMILES: CC(C)NC(=O)c1ccc(Cn2ccc(=O)[nH]c2=O)cc1]

or a pharmaceutically acceptable salt thereof.

18. The method of claim 15, wherein the compound is represented by:

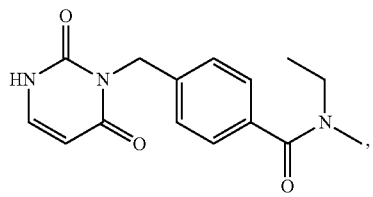 [SMILES: CCN(C)C(=O)c1ccc(Cn2c(=O)cc[nH]c2=O)cc1]

or a pharmaceutically acceptable salt thereof.

19. The method of claim 15, wherein the compound is represented by:

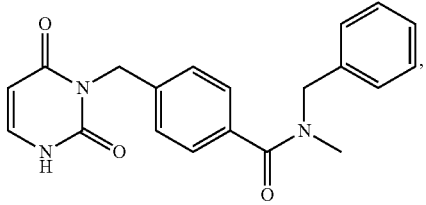 [SMILES: CN(Cc1ccccc1)C(=O)c1ccc(Cn2c(=O)cc[nH]c2=O)cc1]

or a pharmaceutically acceptable salt thereof.

20. The method of claim 15, wherein the compound is represented by:

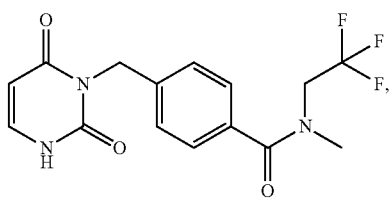 [SMILES: CN(CC(F)(F)F)C(=O)c1ccc(Cn2c(=O)cc[nH]c2=O)cc1]

or a pharmaceutically acceptable salt thereof.

* * * * *